(12) United States Patent
Stulen et al.

(10) Patent No.: US 10,639,058 B2
(45) Date of Patent: May 5, 2020

(54) ULTRASONIC SURGICAL INSTRUMENT WITH FEATURES FOR FORMING BUBBLES TO ENHANCE CAVITATION

(71) Applicant: ETHICON LLC, Guaynabo, PR (US)

(72) Inventors: Foster B. Stulen, Mason, OH (US); Timothy G. Dietz, Wayne, PA (US); Jeffrey D. Messerly, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 167 days.

(21) Appl. No.: 15/693,630

(22) Filed: Sep. 1, 2017

(65) Prior Publication Data

US 2018/0070974 A1 Mar. 15, 2018

Related U.S. Application Data

(62) Division of application No. 14/084,882, filed on Nov. 20, 2013, now Pat. No. 9,763,688.

(51) Int. Cl.
*A61B 17/32* (2006.01)
*A61B 17/22* (2006.01)
*A61B 17/00* (2006.01)

(52) U.S. Cl.
CPC .......... *A61B 17/320068* (2013.01); *A61B 2017/00172* (2013.01); *A61B 2017/00176* (2013.01);
(Continued)

(58) Field of Classification Search
CPC .......... A61B 17/2204; A61B 17/22012; A61B 17/2202; A61B 17/320068;
(Continued)

(56) References Cited

U.S. PATENT DOCUMENTS 2,990,616 A 7/1961 Balamuth et al.
5,322,055 A 6/1994 Davison et al.
(Continued)

FOREIGN PATENT DOCUMENTS

DE 20113290 U1 1/2002
EP 0482847 A1 4/1992
(Continued)

OTHER PUBLICATIONS

International Search Report and Written Opinion dated Apr. 24, 2015 for Application No. PCT/US2014/065411, 20 pgs.
(Continued)

*Primary Examiner* — Ryan J. Severson
(74) *Attorney, Agent, or Firm* — Frost Brown Todd LLC

(57) ABSTRACT

An ultrasonic element comprises an ultrasonic transducer and a head or blade. The ultrasonic transducer is operable to convert electrical power into ultrasonic vibrations. The head or blade is in acoustic communication with the ultrasonic transducer such that the ultrasonic transducer is operable to drive the ultrasonic blade to vibrate ultrasonically. The head or blade has a curved distal face. The curved distal face defines a proximally extending concave curve. The transducer and head or blade may be driven using a control logic that is configured to cause the ultrasonic transducer to generate a first vibration set followed by a second vibration set. The first vibration set is configured to generate microbubbles in a fluid. The second vibration set is configured to grow microbubbles generated by the first vibration set. The control logic may provide a pause between the first vibration set and the second vibration set.

20 Claims, 11 Drawing Sheets

(52) U.S. Cl.
CPC ............... *A61B 2017/22008* (2013.01); *A61B 2017/22024* (2013.01); *A61B 2017/320071* (2017.08); *A61B 2017/320074* (2017.08); *A61B 2017/320084* (2013.01); *A61B 2017/320089* (2017.08); *A61B 2217/007* (2013.01)

(58) Field of Classification Search
CPC ........... A61B 2017/22005; A61B 2017/22007; A61B 2017/22008; A61B 2017/22009; A61B 2017/22024; A61B 2017/22025; A61B 2017/320072; A61B 2017/320076; A61B 2017/32008; A61B 2017/320096; A61H 23/00; A61H 23/0245; A61N 2007/0004; A61N 2007/0008; A61N 2007/003; A61N 2007/0039; A61N 2007/0047; A61N 2007/0056; A61N 2007/0065; A61N 7/00
See application file for complete search history.

(56) References Cited

U.S. PATENT DOCUMENTS

| | | | |
|---|---|---|---|
| 5,324,299 | A | 6/1994 | Davison et al. |
| 5,807,285 | A | 9/1998 | Vaitekunas et al. |
| 5,873,873 | A | 2/1999 | Smith et al. |
| 5,916,192 | A | 6/1999 | Nita et al. |
| 5,980,510 | A | 11/1999 | Tsonton et al. |
| 6,325,811 | B1 | 12/2001 | Messerly |
| 6,328,751 | B1 | 12/2001 | Beaupre |
| 6,423,082 | B1 | 7/2002 | Houser et al. |
| 6,443,969 | B1 | 9/2002 | Novak et al. |
| 6,726,698 | B2* | 4/2004 | Cimino ............... A61B 17/2202 604/22 |
| 6,773,444 | B2 | 8/2004 | Messerly |
| 6,783,524 | B2 | 8/2004 | Anderson et al. |
| 7,316,664 | B2 | 1/2008 | Kadziauskas et al. |
| 7,645,278 | B2 | 1/2010 | Ichihashi et al. |
| 8,057,408 | B2 | 11/2011 | Cain et al. |
| 8,152,825 | B2 | 4/2012 | Madan et al. |
| 8,216,262 | B2 | 7/2012 | O'Donoghue |
| 8,257,377 | B2 | 9/2012 | Wiener et al. |
| 8,348,967 | B2 | 1/2013 | Stulen |
| 8,461,744 | B2 | 6/2013 | Wiener et al. |
| 8,469,981 | B2 | 6/2013 | Robertson et al. |
| 8,531,064 | B2 | 9/2013 | Robertson et al. |
| 8,591,536 | B2 | 11/2013 | Robertson |
| 8,623,027 | B2 | 1/2014 | Price et al. |
| 8,882,791 | B2 | 11/2014 | Stulen |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,044,261 | B2 | 6/2015 | Houser |
| 9,050,124 | B2* | 6/2015 | Houser ............... A61B 17/32006 |
| 9,066,747 | B2* | 6/2015 | Robertson ........ A61B 17/32009 |
| 9,095,367 | B2 | 8/2015 | Olson et al. |
| 9,125,722 | B2 | 9/2015 | Schwartz |
| 9,271,751 | B2 | 3/2016 | Houser et al. |
| 9,381,058 | B2 | 7/2016 | Houser et al. |
| 9,393,037 | B2 | 7/2016 | Olson et al. |
| 9,763,688 | B2 | 9/2017 | Stulen et al. |
| 2003/0093102 | A1* | 5/2003 | Cimino ............... A61B 17/2202 606/169 |
| 2004/0058075 | A1 | 3/2004 | Dahlberg |
| 2006/0079874 | A1 | 4/2006 | Faller et al. |
| 2006/0253050 | A1 | 11/2006 | Yoshimine et al. |
| 2007/0083120 | A1 | 4/2007 | Cain et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2008/0234709 | A1* | 9/2008 | Houser ............ A61B 17/32006 606/169 |
| 2009/0030439 | A1 | 1/2009 | Stulen |
| 2009/0143795 | A1 | 6/2009 | Robertson |
| 2009/0312763 | A1 | 12/2009 | McCormack et al. |
| 2010/0069940 | A1 | 3/2010 | Miller et al. |
| 2011/0087212 | A1 | 4/2011 | Aldridge et al. |
| 2012/0029546 | A1* | 2/2012 | Robertson ........ A61B 17/32009 606/171 |
| 2012/0112687 | A1 | 5/2012 | Houser et al. |
| 2012/0116265 | A1 | 5/2012 | Houser et al. |
| 2013/0012970 | A1* | 1/2013 | Houser ............ A61B 17/32006 606/169 |
| 2013/0116717 | A1 | 5/2013 | Balek et al. |
| 2013/0184711 | A1 | 7/2013 | Rad |
| 2013/0190623 | A1 | 7/2013 | Bertolina et al. |
| 2014/0005701 | A1 | 1/2014 | Olson et al. |
| 2014/0058427 | A1* | 2/2014 | Robertson ........ A61B 17/32009 606/171 |
| 2015/0005774 | A1 | 1/2015 | Voic et al. |
| 2015/0073458 | A1 | 3/2015 | Stoddard et al. |
| 2015/0142033 | A1 | 5/2015 | Stulen et al. |
| 2015/0282834 | A1* | 10/2015 | Robertson ........ A61B 17/32009 606/169 |
| 2018/0070974 | A1* | 3/2018 | Stulen ............ A61B 17/32006 |

FOREIGN PATENT DOCUMENTS

| | | |
|---|---|---|
| WO | WO 03/045468 A1 | 6/2003 |
| WO | WO 2006/110773 A2 | 10/2006 |
| WO | WO 2008/024923 A2 | 2/2008 |
| WO | WO 2012/149837 A1 | 11/2012 |

OTHER PUBLICATIONS

U.S. Appl. No. 13/657,553, filed Oct. 22, 2012.
U.S. Appl. No. 61/410,603, filed Nov. 5, 2010.
Chinese Office Action, The First Office Action, and Search Report dated Mar. 2, 2018 for Application No. CN 201480063565.2, 9 pgs.

* cited by examiner

ULTRASONIC SURGICAL INSTRUMENT WITH FEATURES FOR FORMING BUBBLES TO ENHANCE CAVITATION

This application is a division of U.S. application Ser. No. 14/084,882, filed Nov. 20, 2013, now U.S. Pat. No. 9,763,688, issued on Sep. 19, 2017, entitled "Ultrasonic Surgical Instrument with Features for Forming Bubbles to Enhance Cavitation."

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati. Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued on Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued on Aug. 4, 2015 the disclosure of which is incorporated by reference herein.

Some ultrasonic surgical instruments may include a clamp feature to press tissue against the ultrasonic blade of the end effector. Examples of such an arrangement (sometimes referred to as a clamp coagulator shears or an ultrasonic transector) is disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism." issued Feb. 23, 1999, the disclosure of which is incorporated by reference herein; and U.S. Pat. No. 6,325,811, entitled "Blades with Functional Balance Asymmetries for use with Ultrasonic Surgical Instruments," issued Dec. 4, 2001, the disclosure of which is incorporated by reference herein. Some versions of clamp coagulator shears utilize handles that are either of a pistol or scissors grips design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The operator may thus squeeze a handgrip or other feature to drive a clamp arm, to thereby press the clamp pad toward the blade.

Some ultrasonic devices may be used to provide acoustic cavitation. Acoustic cavitation is a process where vapor/gaseous microbubbles are grown in a host liquid (e.g., water, saline, etc.). The radius of the microbubbles may rise and fall with the acoustic pressure, reaching a peak radius at the peak amplitude of the acoustic pressure and reaching a minimal radius at a zero pressure point. The radius of each microbubble may depend on a variety of factors, including the liquid density, the liquid speed of sound, hydrostatic pressure, acoustic pressure, the ratio of heat capacities, surface tension, liquid viscosity, the hard core radius of the microbubble, and/or other factors. If the ultrasonic acoustic amplitude (particularly the rarefaction pressure) in the liquid is sufficiently high enough, these microbubbles will collapse violently. The violent collapse of the microbubbles may create small but very forceful jets of the liquid. If performed in a patient, such jets may break down adjacent surfaces of tissue and/or other anatomical structures. By way of example only, the velocity of such jets in fat may be approximately 980 meters/second. The velocity of such jets in muscle may be approximately 24 meters/second. The velocity of such jets in cartilage may be approximately 37 meters/second. The velocity of such jets in bone may be approximately 83 meters/second. It should be understood that these values are merely illustrative.

When acoustic cavitation is used to break down soft tissue, the process may be referred to as "histotripsy." Examples of histotripsy techniques and associated technology are described in U.S. Pub. No. 2007/0083120, entitled "Pulsed Cavitational Ultrasound Therapy," published Apr. 12, 2007, the disclosure of which is incorporated by reference herein; U.S. Pub. No. 2013/0190623, entitled "Histotripsy Therapy Transducer," published Jul. 25, 2013, the disclosure of which is incorporated by reference herein; and U.S. Pat. No. 8,057,408, entitled "Pulsed Cavitational Ultrasound Therapy," issued Nov. 15, 2011, the disclosure of which is incorporated by reference herein. A somewhat similar procedure is known as lithotripsy, where shock waves are used to break up kidney stones. Such shock waves may be generated by an ultrasonic transducer.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
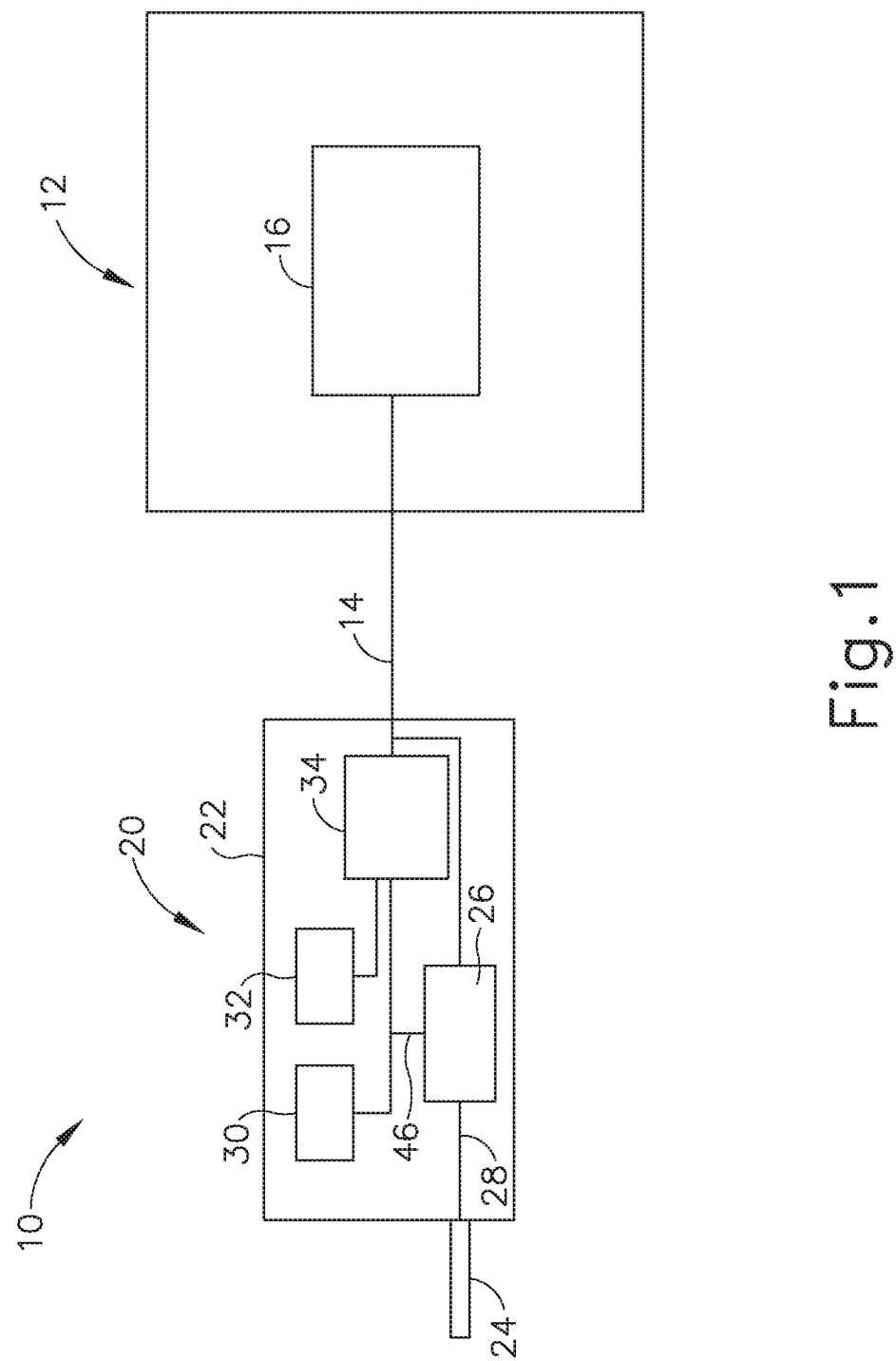
FIG. 1 depicts a block schematic view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04 or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes HF105 and DH105 by Ethicon Endo-Surgery, Inc. of Cincinnati. Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
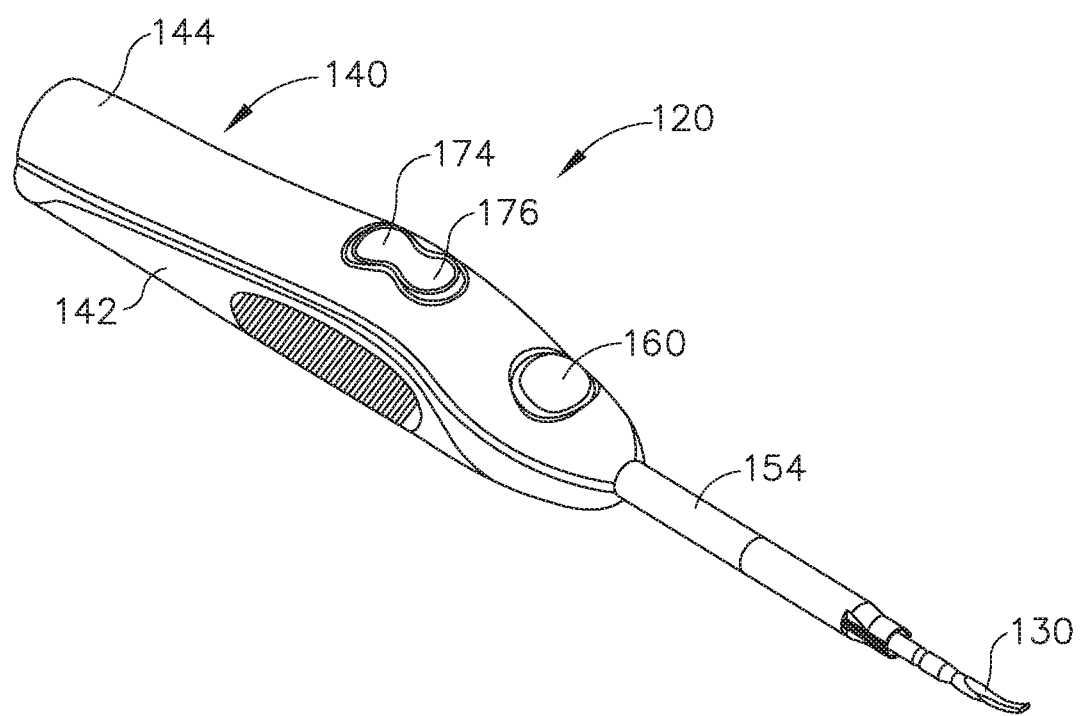
FIG. 2 depicts a perspective view of an exemplary ultrasonic surgical instrument that may form part of the system of FIG. 1.
Figure 3:
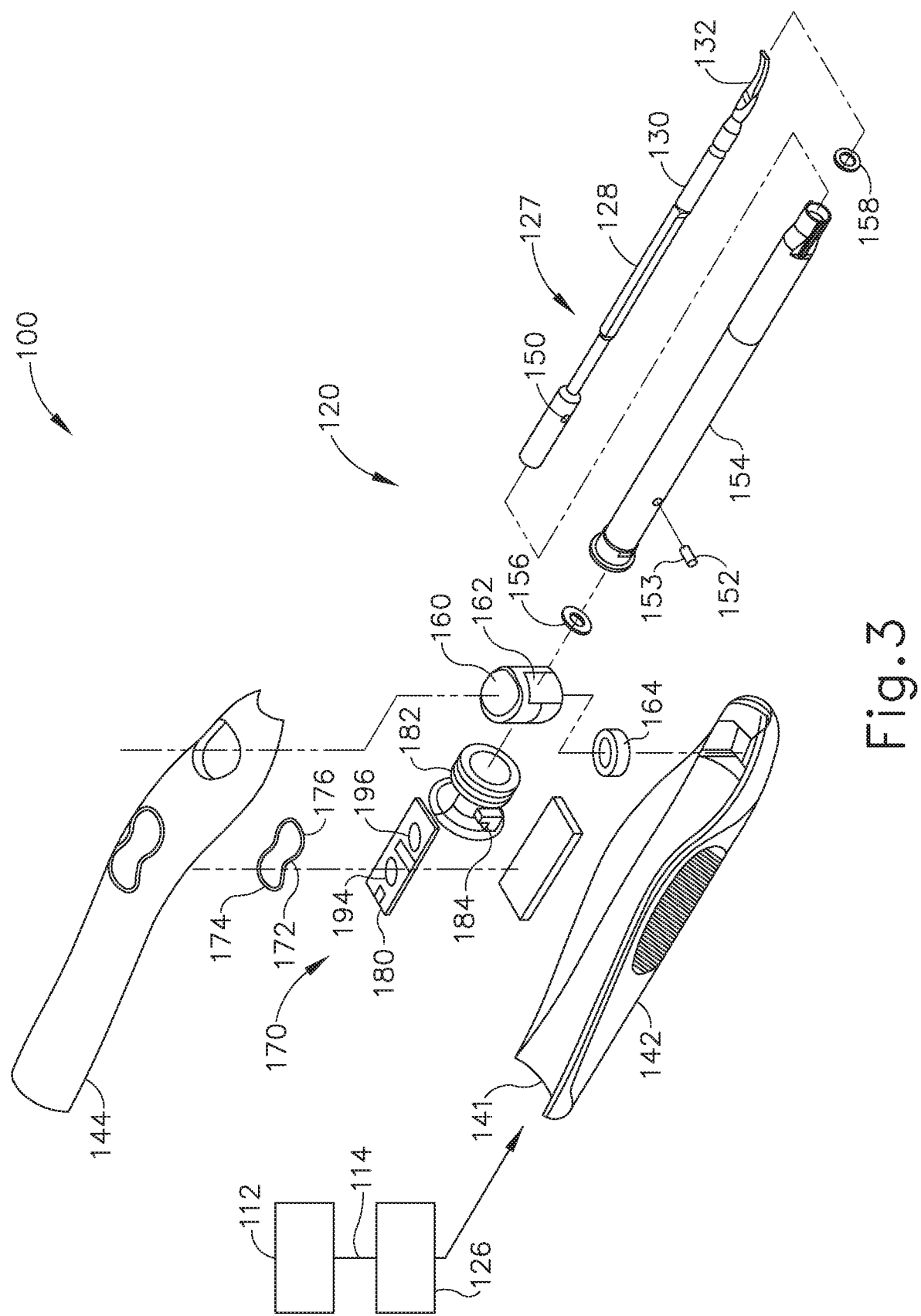
FIG. 3 depicts an exploded view of the instrument of FIG. 2.

FIGS. 2-3 depict an exemplary ultrasonic surgical instrument (120), which is part of an ultrasonic surgical system (100) that includes an ultrasonic transducer (126) coupled with an ultrasonic generator (112) via a cable (114). Instrument (120) also includes an ultrasonic transmission assembly (127), which is mechanically and acoustically coupled with ultrasonic transducer (126). In some versions, ultrasonic transmission assembly (127) is coupled with ultrasonic transducer (126) by a threaded connection, though any other suitable type of coupling may be used. Ultrasonic transmission assembly (127) comprises an ultrasonic waveguide (128) and blade (130). As will be apparent to those of ordinary skill in the art, when ultrasonic transducer (126) is powered by generator (112), ultrasonic transducer (126) produces ultrasonic vibrations, which are communicated to blade (130) via ultrasonic waveguide (128). This causes tip (132) of blade (130) to vibrate at an ultrasonic frequency, allowing blade (130) to be used to cut and coagulate tissue, etc. Thus, generator (112), transducer (126), waveguide (128), and blade (130) operate just like generator (12), transducer (26), waveguide (28), and blade (24) described above.

Instrument (120) of the present example further comprises a multi-piece handle assembly (140) that is configured to substantially isolate the operator from the vibrations of the piezoelectric assembly contained within transducer (126). By way of example only, handle assembly (140) may be shaped to be grasped and manipulated in a pencil-like arrangement. Handle assembly (140) of the present example comprises mating housing portions (142) and (144). While a multi-piece handle assembly (140) is illustrated, handle assembly (140) may alternatively comprise a single or unitary component. Handle assembly (140) may be constructed from a durable plastic, such as polycarbonate or a liquid crystal polymer. It is also contemplated that handle assembly (140) may alternatively be made from a variety of materials or combinations of materials, including but not limited to other plastics, ceramics, and/or metals, etc. In some versions, the proximal end of instrument (120) receives and is fitted with ultrasonic transducer (126) by insertion of ultrasonic transducer (126) into handle assembly (140). Instrument (120) may be attached to and removed from ultrasonic transducer (126) as a unit. The elongated transmission assembly (127) of the instrument (120) extends orthogonally from instrument handle assembly (140).

Ultrasonic waveguide (128), which is configured to transmit ultrasonic energy from transducer (126) to the tip (132) of blade (130), may be flexible, semi-flexible or rigid. Ultrasonic waveguide (128) may also be configured to amplify the mechanical vibrations transmitted through ultrasonic waveguide (128) to blade (130). Ultrasonic waveguide (128) may further include at least one radial aperture (150) extending therethrough, substantially perpendicular to the longitudinal axis of ultrasonic waveguide (128). Aperture (150) is located at a longitudinal position corresponding to a node associated with ultrasonic vibrations communicated along waveguide (128). Aperture (150) is configured to receive a connector pin (152), discussed below, which connects ultrasonic waveguide (128) to an outer sheath (154). Proximal o-ring (156) and distal o-ring (158) are assembled onto transmission assembly (127) near longitudinal positions corresponding to nodes associated with ultrasonic vibrations communicated along waveguide (128) in the present example, though various other components or configurations may be used.

Blade (130) may be integral with ultrasonic waveguide (128) and formed as a single unit. In some versions, blade (130) may be connected by a threaded connection, a welded joint, and/or some other coupling feature(s). The distal end of blade (130), or blade tip (132), is disposed at or near a longitudinal position corresponding to an anti-node associated with ultrasonic vibrations communicated along waveguide (128) and blade (130) in order to tune the acoustic assembly to a preferred resonant frequency $f_o$ when the acoustic assembly is not loaded by tissue. When ultrasonic transducer (126) is energized, blade tip (132) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. Blade tip (132) may also vibrate in the y-axis at about 1 to about 10 percent of the motion in the x-axis. Of course, movement of blade tip (132) may alternatively have any other suitable characteristics. By way of example only, blade tip (132) may vibrate with more movement in the y-axis than in the x-axis. As another merely illustrative example, blade tip (132) may vibrate in the y-axis at up to about 50 percent of the motion in the x-axis. Other suitable vibrational characteristics will be apparent to those of ordinary skill in the art in view of the teachings herein.

Ultrasonic waveguide (128) is positioned within outer sheath (154) and held in place via pin (152). Pin (152) may be made of any compatible metal, such as stainless steel or titanium or a durable plastic, such as polycarbonate or a liquid crystal polymer. Alternatively, any other suitable material or combination of materials may be used. In some versions, pin (152) is partially coated with an elastomeric material, such as silicon, etc., for that portion (153) of pin (152) that extends through ultrasonic waveguide (128). Elastomeric material may provide insulation from the vibrating blade throughout the length of hole (152). In some settings, this may enable high efficiency operation whereby minimal overheating is generated and maximum ultrasonic output power is available at blade tip (132) for cutting and coagulation, etc. Of course, such elastomeric material is merely optional.

Outer sheath (154) passes through an aperture (162) of release button (160). A spring (164) is positioned below release button (160) and resiliently biases release button (160) upwardly. The upward force imposed by spring (164) causes the perimeter of aperture (162) to firmly assert pressure against outer sheath (154), and thereby selectively prevents outer sheath (154), ultrasonic waveguide (128), and blade (130) from either rotating within handle (140) or axially translating with respect to handle (140). When the operator exerts a downward force on release button (160), spring (164) is compressed and it no longer asserts a holding force on outer sheath (154). The operator may then axially translate outer sheath (154), ultrasonic waveguide (128), and blade (130) relative to handle (140) and/or rotate outer sheath (154), ultrasonic waveguide (128), and blade (130) relative to handle (140). Accordingly, it should be understood that the longitudinal and/or rotational position of blade (130) relative to handle (140) may be selectively adjusted by the operator while depressing release button (160), while still allowing blade (130) to vibrate ultrasonically at such selected positions, allowing blade (130) to be used in various surgical procedures at such selected positions. To initiate such ultrasonic action of blade (130), the operator may operate a footswitch (not shown), activate a pushbutton (174, 176) as described below, activate a button on generator (112), or perform some other act on some component of system (100).

In the present example, housing of handle (140) includes a proximal end, a distal end, and a cavity (141) extending longitudinally therein. Cavity (141) is configured to accept a switch assembly (170) and at least a portion of ultrasonic transducer assembly (126). In one some versions, the distal end of ultrasonic transducer assembly (126) threadably attaches to the proximal end of ultrasonic waveguide (128), though any other suitable type of coupling may be used. Electrical contacts of ultrasonic transducer (126) also interface with switch assembly (170) to provide the operator with finger-activated controls on surgical instrument (120). Ultrasonic transducer (126) of the present example includes two conductive rings (not shown) which are securely disposed within the body of ultrasonic transducer (126) as is described in U.S. Pub. No. 2007/0106158, entitled "Medical Ultrasound System and Handpiece and Methods for Making and Tuning," published May 10, 2007, now U.S. Pat. No. 8,152,825, issued on Apr. 10, 2012, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (140) by way of corresponding supporting mounts on switch housing (182) and housing portions (142, 144).

Pushbutton assembly (172) of the present example comprises pushbuttons (174, 176). Circuit assembly (180) provides for the electro-mechanical interface between pushbuttons (174, 176) and generator (112) via ultrasonic transducer (126). Circuit assembly (180) comprises two dome switches (194, 196) that are mechanically actuated by depressing pushbuttons (174, 176) respectively. Dome switches (194, 196) are electrical contact switches, that when depressed provide an electrical signal to generator (112). Pins (not shown) are electrically connected to dome switches (194, 196). In particular, one end of each pin is electrically connected to a corresponding dome switch (194, 196). The other end of each pin is electrically connected with a corresponding ring conductor at the distal end of ultrasonic transducer (126). That is, the pins each have spring-loaded tips that interface with ultrasonic transducer (126) in a manner similar to that described above. Circuit assembly (180) also comprises two diodes within a diode package (not shown) that connect to the pins, respectively. While the pins provide electrical contact to the ring conductors of ultrasonic transducer, the ring conductors are in turn connected to conductors in cable (114) that connects to generator (112). Of course a variety of alternative configurations may be used.

By depressing pushbuttons (174, 176), the corresponding contact surfaces depress corresponding dome switches (194, 196) to selectively activate the circuit (180). For instance, when the operator depresses pushbutton (174), generator (112) may respond with a certain energy level, such as a maximum ("max") power setting. When the operator depresses pushbutton (176), generator (112) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability.

In addition to or in lieu of being constructed in accordance with the above teachings, at least part of instrument (120) may be constructed and operable in accordance with at least some of the teachings of U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037; U.S. patent application Ser. No. 13/657,553 now U.S. Pat. No. 9,095,367; and/or U.S. Pat. App. No. 61/410,603. The disclosures of each of the foregoing patents, publications, and applications are incorporated by reference herein. It should also be understood that instrument (120) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (120) may have various structural and functional similarities with the devices taught in any of the other references that are cited and incorporated by reference herein. Additional merely illustrative variations for instrument (120) will be apparent to those of ordinary skill in the art in view of the teachings herein. It should be understood that the below described variations may be readily applied to instrument (120) described above and any of the instruments referred to in any of the references that are cited herein, among others.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (20), there is no intent for any of the description herein to be presumed as admitted prior art. Several teachings herein in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

III. Exemplary Ultrasonic Blade Variations

As noted above, an ultrasonic device may be used to provide acoustic cavitation, to thereby break down tissue, such as in a histotripsy process. Such a process may be carried out in accordance with at least some of the teachings of U.S. Pub. No. 2007/0083120, U.S. Pub. No. 2013/0190623, and/or U.S. Pat. No. 8,057,408, the disclosures of which are incorporated by reference herein. It should be understood that ultrasonic vibrations may sufficiently grow and collapse microbubbles or vapor voids within just a couple or few ultrasonic cycles. In some instances, acoustic cavitation may be used in an orthopedic context on tissues other than soft tissues. In particular, acoustic cavitation may be used to precisely remove fibrous tissue (e.g., at least part of the annulus of a spinal disc), cartilage (e.g., articular cartilage of joints), and/or bone (e.g., cutting joints to prepare for artificial joint replacements, cutting the lamina of a vertebra, etc.). By way of illustration only, acoustic cavitation may be used to erode or remove the fibrous annulus of a spinal disc without significantly impacting adjacent bone, in response to degenerative disc disease or for any other clinical reason. Still other ways and clinical settings in which acoustic cavitation may be used will be apparent to those of ordinary skill in the art in view of the teachings herein.

The examples described below include variations of ultrasonic blades that may be used to provide acoustic cavitation. It should be understood that the blades described below may be used as substitutes for blades (24, 130) described above. In other words, the blades described below may be readily incorporated into instruments (10, 120) described above. To the extent that such incorporation of the below described blades may warrant additional modifications to instruments (10, 120), examples of such modifications will be apparent to those of ordinary skill in the art in view of the teachings herein. By way of example only, generator (12, 112) may be tuned to drive transducer (26, 126) with a power profile that produces acoustic vibrations providing an appropriately high mechanical index and thermal index through the blade. In some instances, the thermal index is lower than the thermal index that would be encountered in a conventional high-intensity focused ultrasound (HIFU) operation. Cavitation effects may be increased by increasing the frequency of the ultrasonic vibrations, introducing seed microbubbles, increasing surface tension in the fluid, and/or in other ways. It should also be understood that the blades described below need not contact the tissue surface where the acoustic cavitation erodes the tissue. In other words, the acoustic cavitation effects may occur at a tissue surface or tissue region that is spaced away from surfaces of the blade. The blades described below may thus be viewed as effectively constituting transducer heads. In other words, the use of the term "blade" should not be understood to require direct contact between the blade structure and the tissue surface or region where the blade provides cavitation effects.

Any of the examples below may be used to provide and/or drive cavitation microbubbles within a liquid that is substantially standing in relation to the tissue or other anatomical structure where the erosion is intended. In addition or in the alternative, a source of moving fluid may be used to drive the fluid, such that the motion in the fluid carries the microbubbles into engagement with the tissue or other anatomical structure where the erosion is intended. In some instances, the fluid may be driven at a high velocity such that the driven motion of the fluid itself may assist in further eroding the tissue or other anatomical structure. Some merely illustrative examples of how a fluid flow may be introduced in conjunction with an ultrasonic cavitation blade will be described in greater detail below, while other examples will be apparent to those of ordinary skill in the art in view of the teachings herein.

A. Exemplary Ultrasonic Blade with Transverse Opening

Figure 4:
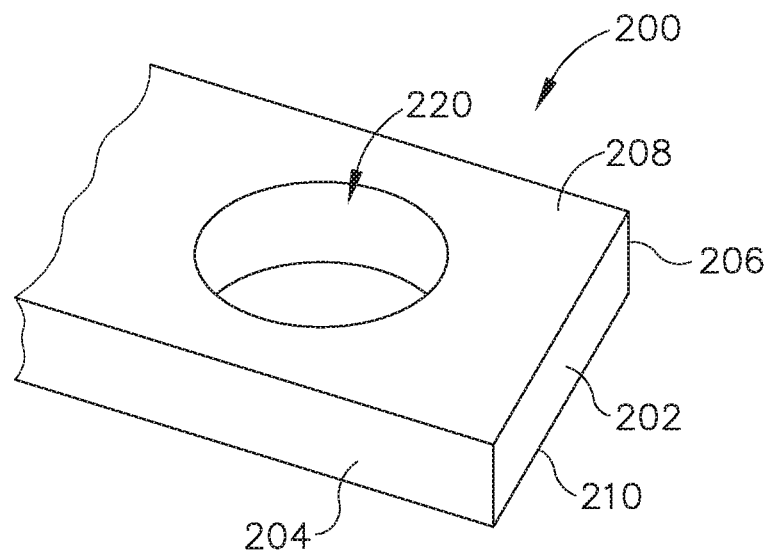
FIG. 4 depicts a perspective view of the distal end of an exemplary alternative ultrasonic blade that may be incorporated into the instrument of FIG. 2.
Figure 5:
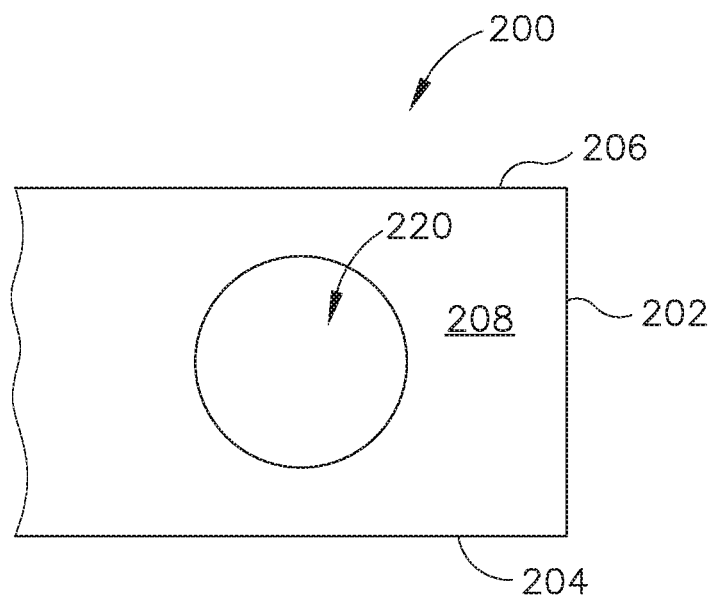
FIG. 5 depicts a top plan view of the distal end of the ultrasonic blade of FIG. 4.

FIGS. 4-5 show an exemplary alternative ultrasonic blade (200) that may be readily incorporated into instrument (20, 120). In particular, blade (200) may be mechanically and acoustically coupled with waveguide (28, 128) in place of blade (24, 132). Blade (200) of this example comprises a flat distal face (202), flat side faces (204, 206), a flat upper face (208), and a flat lower face (210). Upper face (208) and lower face (210) are both broader than side faces (204, 206). Blade (200) of this example thus has a rectangular cross-sectional profile. It should be understood, however, that any one or more of surfaces (202, 204, 206, 208, 210) may instead by curved and/or have other characteristics.

Blade (200) of this example further includes an opening (220) extending from face (208) to face (210). Opening (220) is located proximal to distal face (202). A column of liquid (e.g., saline, etc.) may be driven through opening (220), such that the column of liquid serves as a medium for ultrasonic waves generated through blade (200). When blade (200) is activated to vibrate at ultrasonic frequencies, blade (200) may generate compression/pressure waves that are directed radially inwardly within opening (220). It should be understood that these inwardly directed waves may produce cavitation effects with liquid disposed in opening (200). Such cavitation effects may erode tissue or other anatomical structures that is/are encountered by liquid that is disposed in opening (200) or that passes through opening (200). In some instances, an additional feature is used to drive liquid through opening (200) along a path that is generally transverse to blade (200). Such motion in the liquid may carry microbubbles that are enlarged by the compression waves in opening (220) away from opening (220), such that the enlarged microbubbles burst to provide cavitation effects after the microbubbles leave opening (220). Various suitable flow rates for driving fluid through opening (220) will be apparent to those of ordinary skill in the art in view of the teachings herein.

Opening (220) of the present example has a circular shape. However, it should be understood that opening (220) may instead have some other shape. It should also be understood that blade (200) may include an integral fluid conduit (e.g., a fluid passageway formed as a bore extending through the body of blade (200)). Such a fluid conduit may terminate at opening (220). Such a fluid conduit may be used to introduce seed microbubbles within opening (220). In addition or in the alternative, such a fluid conduit may be used to provide a flow of fluid through opening (220), to promote migration of microbubbles that are enlarged in opening (220) out of opening (220). Other variations of blade (200) will be apparent to those of ordinary skill in the art in view of the teachings herein.

B. Exemplary Ultrasonic Blade with Curved Distal Face

Figure 6:
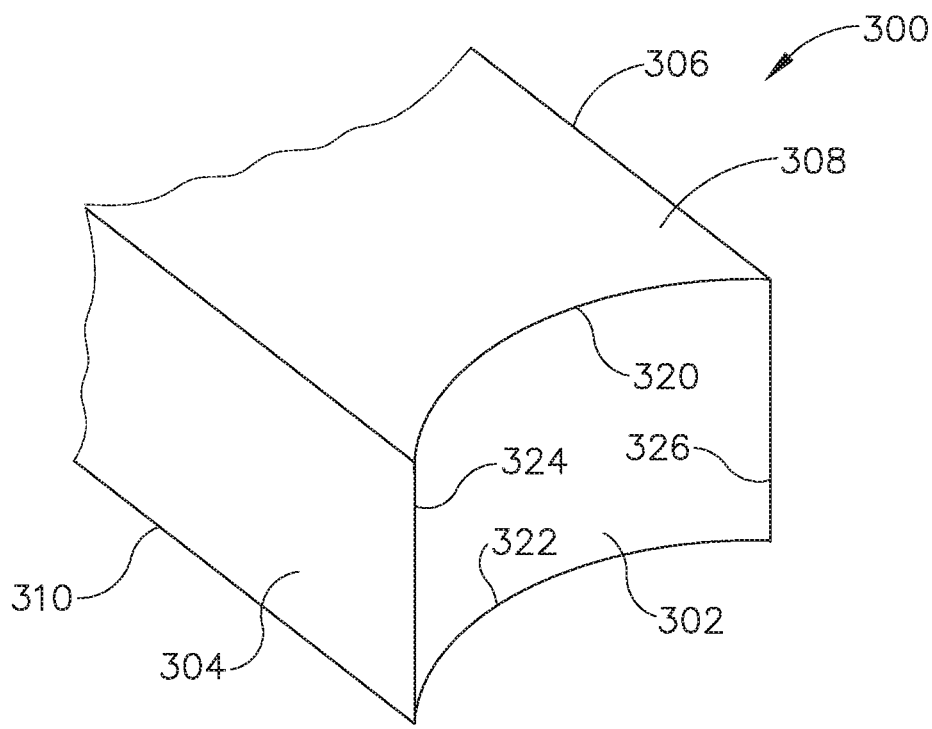
FIG. 6 depicts a perspective view of the distal end of another exemplary alternative ultrasonic blade that may be incorporated into the instrument of FIG. 2.
Figure 7:
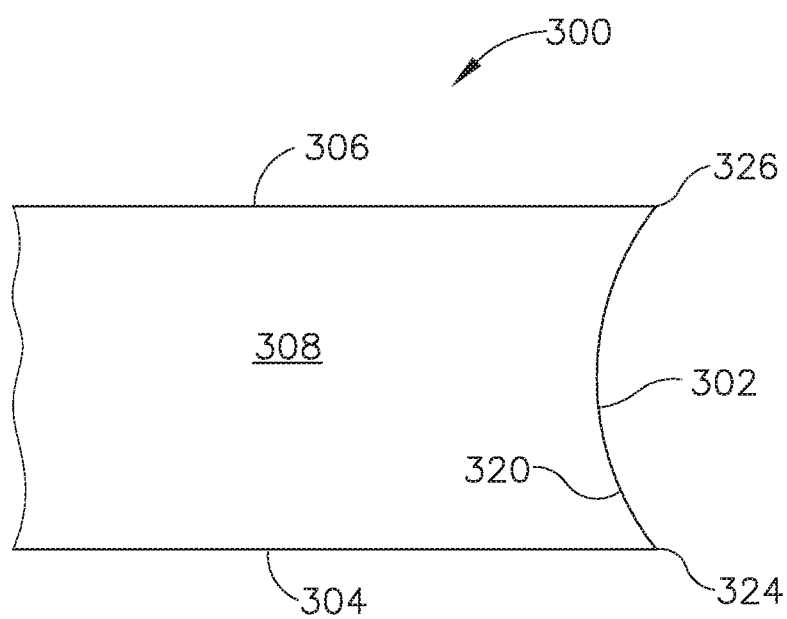
FIG. 7 depicts a top plan view of the distal end of the ultrasonic blade of FIG. 6.
Figure 8:
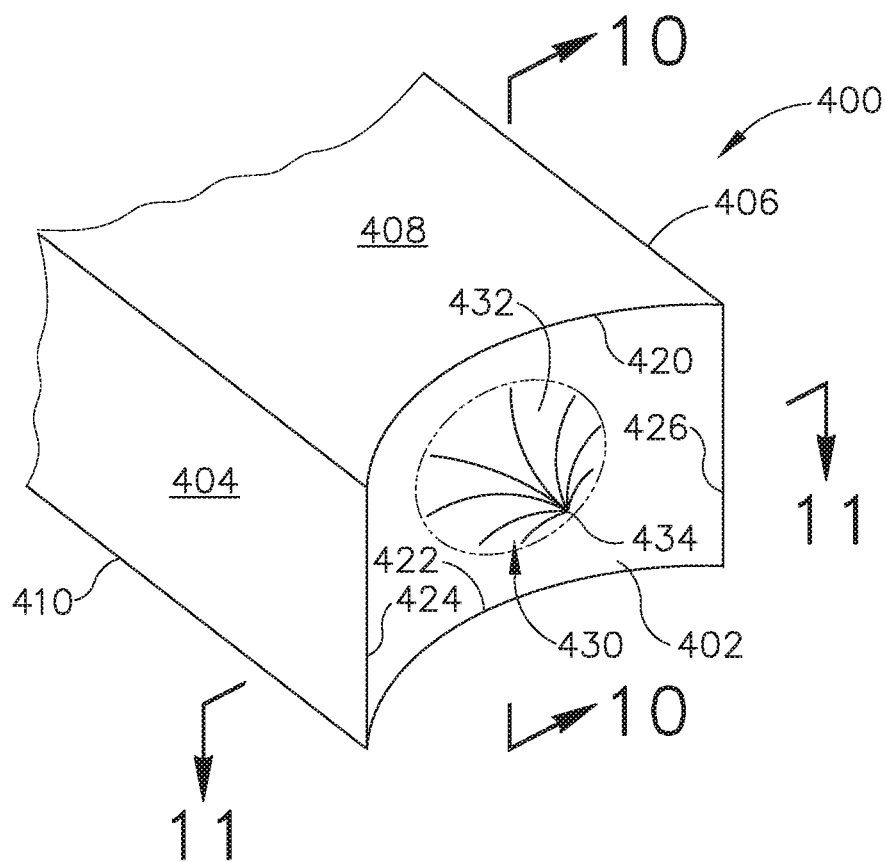
FIG. 8 depicts a perspective view of the distal end of another exemplary alternative ultrasonic blade that may be incorporated into the instrument of FIG. 2.

FIGS. 6-7 show another exemplary alternative ultrasonic blade (300) that may be readily incorporated into instrument (20, 120). In particular, blade (300) may be mechanically and acoustically coupled with waveguide (28, 128) in place of blade (24, 132). Blade (300) of this example comprises a curved distal face (302), flat side faces (304, 306), a flat upper face (308), and a flat lower face (310). It should be understood that any one or more of surfaces (304, 306, 308, 310) may instead by curved and/or have other characteristics.

The body of ultrasonic blade (300) defines a central longitudinal axis. This axis extends through a center, proximal-most point on curved distal face (302). In the present example, the curvature of distal face (302) provides a curved upper edge (320) at the transition between distal face (302) and upper face (308). The curvature of distal face (302) also provides a curved lower edge (322) at the transition between distal face (302) and lower face (310). However, straight edges (324, 326) are provided at the transition between distal face (302) and respective side faces (304, 306). It should be understood from the foregoing that distal face (302) curves along one plane (i.e., a plane that is parallel to upper and lower faces (308, 310)) in this example. In some versions, the curvature of distal face (302) is defined by a single radius of consistent length, such that distal face (302) has an arc-shaped profile. In some other versions, the curvature of distal face (302) is parabolic. In still other versions, the curvature of distal face (302) is hyperbolic. Other suitable configurations for distal face (302) will be apparent to those of ordinary skill in the art in view of the teachings herein.

When blade (300) is activated with ultrasonic vibrations, the curvature of distal face (302) may result in cavitation effects at a particular point or region that is spaced distally from distal face (302). For instance, in versions where distal face (302) has an arc-shaped profile, the cavitation effects generated by activated blade (300) may be focused at the origin of the radius that defines the arc-shaped profile of distal face (302). In versions where distal face (302) has a parabolic profile, the cavitation effects generated by activated blade (300) may be focused at the focus of the parabola that defines the parabolic profile of distal face (302). In versions where distal face (302) has a hyperbolic profile, the cavitation effects generated by activated blade (300) may be focused at the focus of the hyperbola that defines the hyperbolic profile of distal face (302). Other suitable locations at which cavitation effects generated by activated blade (300) may be focused will be apparent to those of ordinary skill in the art in view of the teachings herein.

As noted above with respect to blade (200), blade (300) of this example may include an integral fluid conduit (e.g., a fluid passageway formed as a bore extending through the body of blade (300)). Such a fluid conduit may terminate at distal face (302). Such a fluid conduit may be used to introduce seed microbubbles in front of distal face (302). In addition or in the alternative, such a fluid conduit may be used to provide a flow of fluid distally from distal face (302), to promote migration of microbubbles that are enlarged by blade (300) distally toward tissue or some other anatomical structure that ids distally spaced away from distal face (302). Other variations of blade (300) will be apparent to those of ordinary skill in the art in view of the teachings herein.

C. Exemplary Ultrasonic Blade with Curved Distal Face and Focus Point

FIGS. 8-11 show another exemplary alternative ultrasonic blade (400) that may be readily incorporated into instrument (20, 120). In particular, blade (400) may be mechanically and acoustically coupled with waveguide (28, 128) in place of blade (24, 132). Blade (400) of this example comprises a pointed distal face (402), flat side faces (404, 406), a flat upper face (408), and a flat lower face (410). It should be understood that any one or more of surfaces (404, 406, 408, 410) may instead by curved and/or have other characteristics. In the present example, the curvature of distal face (402) provides a curved upper edge (420) at the transition between distal face (402) and upper face (408). The curvature of distal face (402) also provides a curved lower edge (422) at the transition between distal face (402) and lower face (410). However, straight edges (424, 426) are provided at the transition between distal face (402) and respective side faces (404, 406).

Figure 9:
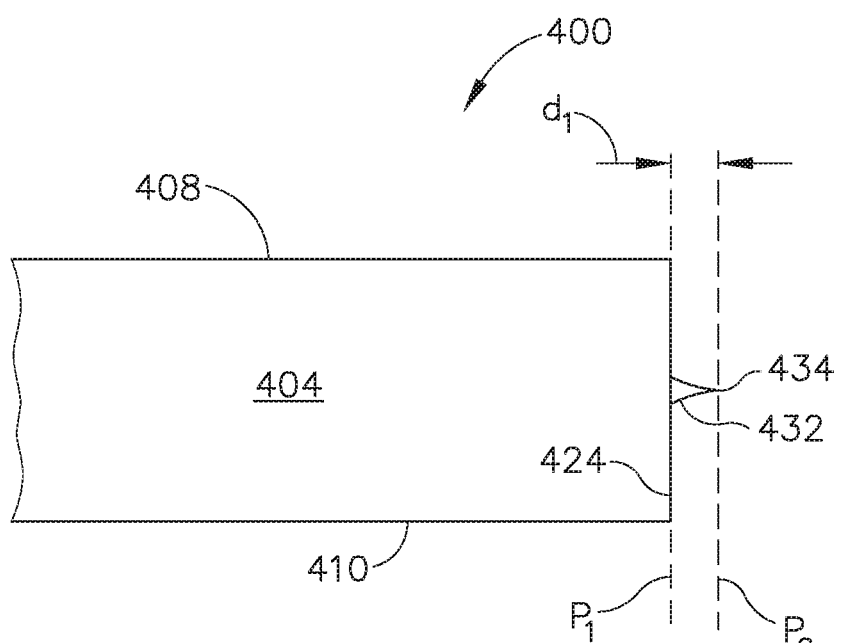
FIG. 9 depicts a top plan view of the distal end of the ultrasonic blade of FIG. 8.
Figure 10:
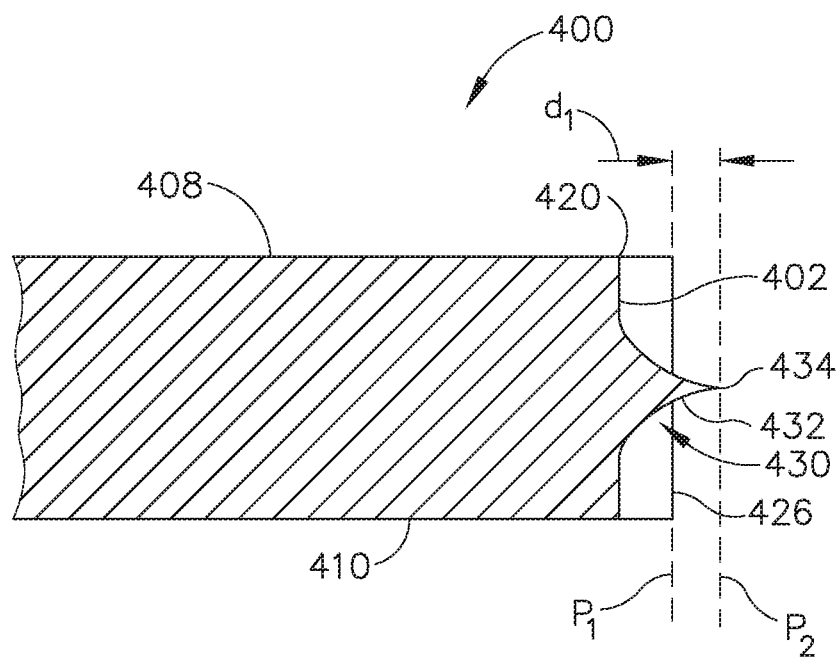
FIG. 10 depicts a side cross-sectional view of the distal end of the ultrasonic blade of FIG. 8, taken along line 10-10 of FIG. 8.
Figure 11:
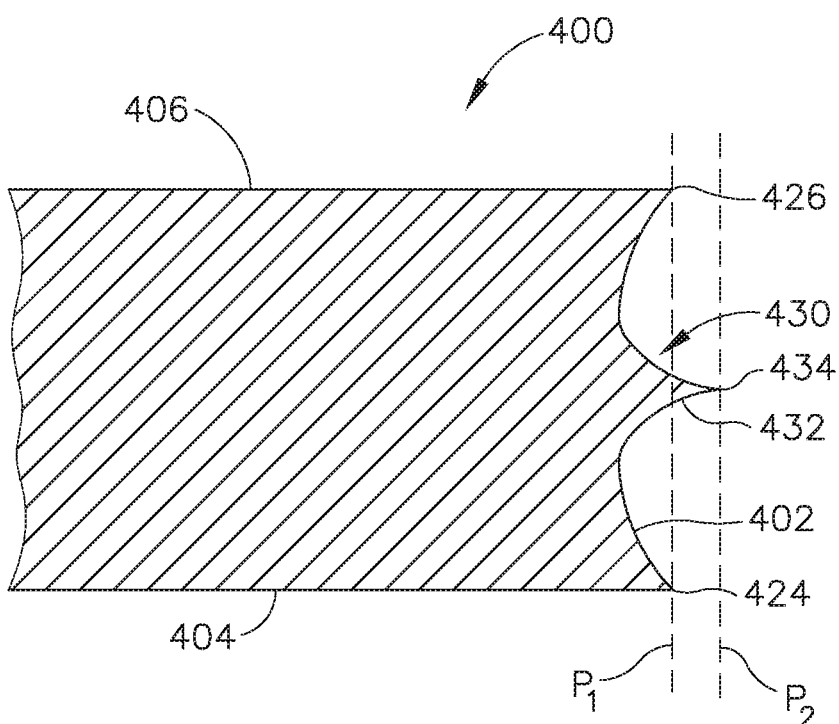
FIG. 11 depicts a top cross-sectional view of the distal end of the ultrasonic blade of FIG. 8, taken along line 11-11 of FIG. 8.

Pointed distal face (402) of this example includes a pointed region (430) located at the center of pointed distal face (402). Pointed region comprises a sharply curved surface (432) that terminates in a sharp point (434). The body of ultrasonic blade (400) defines a central longitudinal axis. This axis extends through sharp point (434). As best seen in FIGS. 9-11, edges (424, 426) of blade (400) are positioned at a first transverse plane ($P_1$) while sharp point (434) is positioned at a second transverse plane ($P_2$). Second transverse plane ($P_2$) is distally spaced from first transverse plane ($P_1$) by a distance ($d_1$). In some versions, second transverse plane ($P_2$) is distally spaced from first transverse plane ($P_1$), such that sharp point (434) is recessed relative to edges (424, 426). In still other versions, sharp point (434) and edges (424, 426) are located on the same transverse plane ($P_1$).

As best seen in FIGS. 10-11, curved surface (432) of pointed region (430) has a curvature that differs from the curvature of the rest of distal face (402). In particular, the region of distal face (402) that is outside of pointed region (430) curves along one plane (i.e., a plane that is parallel to upper and lower faces (408, 410)) in this example. In some versions, the curvature of this particular region of distal face (402) is defined by a single radius of consistent length, such that distal face (402) has an arc-shaped profile. In some other versions, the curvature of this particular region of distal face (402) is parabolic. In still other versions, the curvature of this particular region of distal face (402) is hyperbolic. Other suitable configurations for this particular region of distal face (402) will be apparent to those of ordinary skill in the art in view of the teachings herein.

Curved surface (432) of pointed region (430) curves along two planes (i.e., a plane that is parallel to upper and lower faces (408, 410) and a plane that is parallel to side faces (404, 406)) in this example. The curvature of curved surface (432) along one of those planes may be similar to the curvature of curved surface (432) along the other one of those planes. For instance, the curvature of curved surface (432) along the plane that is parallel to upper and lower faces (408, 410) may have an arc-shaped profile; while the curvature of curved surface (432) along the plane that is parallel to side faces (404, 406) may also have an arc-shaped profile. In such versions, the same radius length may be used to define the curves along these two planes. Alternatively, the radius length may differ for each plane. Similarly, the curvature of curved surface (432) along the plane that is parallel to upper and lower faces (408, 410) may have a parabolic profile; while the curvature of curved surface (432) along the plane that is parallel to side faces (404, 406) may also have a parabolic profile. The characteristics of the parabolas defining these curves may be the same or different from each other. As yet another merely illustrative example, the curvature of curved surface (432) along the plane that is parallel to upper and lower faces (408, 410) may have a hyperbolic profile; while the curvature of curved surface (432) along the plane that is parallel to side faces (404, 406) may also have a hyperbolic profile. The characteristics of the hyperbolas defining these curves may be the same or different from each other.

Of course, the curvature of curved surface (432) along the plane that is parallel to upper and lower faces (408, 410) may alternatively be of a completely different character than the curvature of curved surface (432) along the plane that is parallel to side faces (404, 406). For instance, the curvature of curved surface (432) along the plane that is parallel to upper and lower faces (408, 410) may have an arc-shaped profile; while the curvature of curved surface (432) along the plane that is parallel to side faces (404, 406) has a parabolic profile or a hyperbolic profile. As another merely illustrative example, the curvature of curved surface (432) along the plane that is parallel to upper and lower faces (408, 410) may have a parabolic profile; while the curvature of curved surface (432) along the plane that is parallel to side faces (404, 406) has an arc-shaped profile or a hyperbolic profile. As yet another merely illustrative example, the curvature of curved surface (432) along the plane that is parallel to upper and lower faces (408, 410) may have a hyperbolic profile; while the curvature of curved surface (432) along the plane that is parallel to side faces (404, 406) has an arc-shaped profile or a parabolic profile. Other suitable variations and configurations for curved surface (432) will be apparent to those of ordinary skill in the art in view of the teachings herein.

In the present example, the configuration of pointed region (430) may provide a very intense acoustic pressure at tip (434), which may cause initiation of microbubble formation for enhanced cavitation. In other words, tip (434) may generate "seed" microbubbles, which are then expanded by the surrounding pressure field that is focused at tip (434). In some versions tip (434), curved surface (432), and/or the rest of distal face (402) include(s) carbon, magnesium, and/or an artificial agent such as a surfactant, which may help generate cavitation. In some versions (434) is formed to present a flat distal surface. In some other versions, tip (434) is rounded. In still other versions, tip (434) is sacrificial. In still other versions, tip (434) is substantially sharp, formed by the natural convergence of curved surface (432). As yet another merely illustrative variation, tip (434) may include an orifice that is in fluid communication with a conduit that extends along the length of blade (400). This conduit and orifice may be used to communicate a gas through tip (434) to assist in microbubble seeding. In addition or in the alternative, the conduit and orifice may be used to communicate a liquid through tip (434) to assist in driving the microbubbles distally away from tip (434). Other suitable ways in which tip (434) may be formed and used will be apparent to those of ordinary skill in the art in view of the teachings herein.

Figure 12:
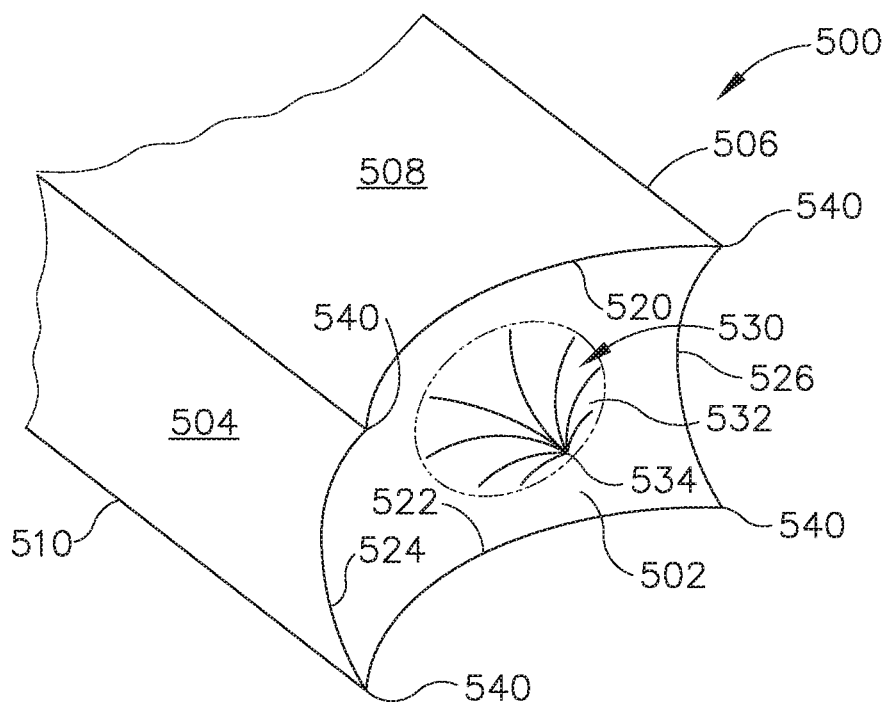
FIG. 12 depicts a perspective view of the distal end of another exemplary alternative ultrasonic blade that may be incorporated into the instrument of FIG. 2.
Figure 13:
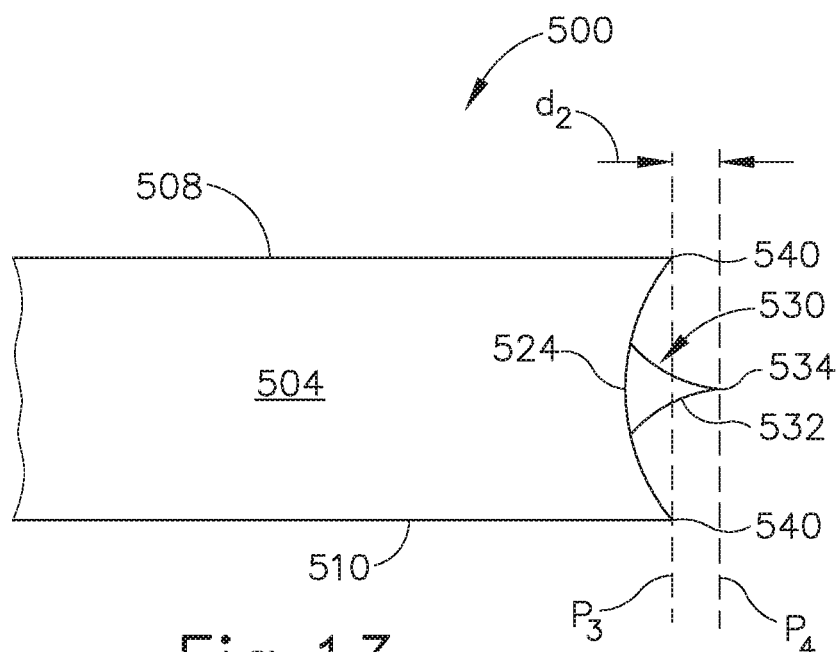
FIG. 13 depicts a top plan view of the distal end of the ultrasonic blade of FIG. 12.

FIGS. 12-13 show another exemplary alternative ultrasonic blade (500) that may be readily incorporated into instrument (20, 120). In particular, blade (500) may be mechanically and acoustically coupled with waveguide (28, 128) in place of blade (24, 132). Blade (500) is substantially similar to blade (400) described above. Blade (500) of this example comprises a pointed distal face (502), flat side faces (504, 506), a flat upper face (508), and a flat lower face (510). It should be understood that any one or more of surfaces (504, 506, 508, 510) may instead by curved and/or have other characteristics. In the present example, the curvature of distal face (502) provides a curved upper edge (520) at the transition between distal face (502) and upper face (508). The curvature of distal face (502) also provides a curved lower edge (522) at the transition between distal face (502) and lower face (510). However, straight edges (524, 526) are provided at the transition between distal face (502) and respective side faces (504, 506).

Pointed distal face (502) of this example includes a pointed region (530) located at the center of pointed distal face (502). Pointed region comprises a sharply curved surface (532) that terminates in a sharp point (534). The body of ultrasonic blade (500) defines a central longitudinal axis. This axis extends through sharp point (534). As best seen in FIG. 13, edges (524, 526) of blade (500) are positioned at a first transverse plane ($P_3$) while sharp point (534) is positioned at a second transverse plane ($P_4$). Second transverse plane ($P_4$) is distally spaced from first transverse plane ($P_3$) by a distance ($d_2$). In some versions, second transverse plane ($P_4$) is distally spaced from first transverse plane ($P_3$), such that sharp point (534) is recessed relative to edges (524, 526). In still other versions, sharp point (534) and edges (524, 526) are located on the same transverse plane ($P_3$).

Curved surface (532) of pointed region (530) has a curvature that differs from the curvature of the rest of distal face (502). In particular, the region of distal face (502) that is outside of pointed region (530) curves along two planes (i.e., a plane that is parallel to upper and lower faces (508, 510) and a plane that is parallel to side faces (504, 506)) in this example. The curvature of this particular region of distal face (502) along one of those planes may be similar to the curvature of this particular region of distal face (502) along the other one of those planes. For instance, the curvature of this particular region of distal face (502) along the plane that is parallel to upper and lower faces (508, 510) may have an arc-shaped profile; while the curvature of this particular region of distal face (502) along the plane that is parallel to side faces (504, 506) may also have an arc-shaped profile. In such versions, the same radius length may be used to define the curves along these two planes. Alternatively, the radius length may differ for each plane. Similarly, the curvature of this particular region of distal face (502) along the plane that is parallel to upper and lower faces (508, 510) may have a parabolic profile; while the curvature of this particular region of distal face (502) along the plane that is parallel to side faces (504, 506) may also have a parabolic profile. The characteristics of the parabolas defining these curves may be the same or different from each other. As yet another merely illustrative example, the curvature of this particular region of distal face (502) along the plane that is parallel to upper and lower faces (508, 510) may have a hyperbolic profile; while the curvature of this particular region of distal face (502) along the plane that is parallel to side faces (504, 506) may also have a hyperbolic profile. The characteristics of the hyperbolas defining these curves may be the same or different from each other.

Of course, the curvature of distal face (502) along the plane that is parallel to upper and lower faces (508, 510) may alternatively be of a completely different character than the curvature of this particular region of distal face (502) along the plane that is parallel to side faces (504, 506). For instance, the curvature of this particular region of distal face (502) along the plane that is parallel to upper and lower faces (508, 510) may have an arc-shaped profile; while the curvature of this particular region of distal face (502) along the plane that is parallel to side faces (504, 506) has a parabolic profile or a hyperbolic profile. As another merely illustrative example, the curvature of this particular region of distal face (502) along the plane that is parallel to upper and lower faces (508, 510) may have a parabolic profile; while the curvature of this particular region of distal face (502) along the plane that is parallel to side faces (504, 506) has an arc-shaped profile or a hyperbolic profile. As yet another merely illustrative example, the curvature of this particular region of distal face (502) along the plane that is parallel to upper and lower faces (508, 510) may have a hyperbolic profile; while the curvature of this particular region of distal face (502) along the plane that is parallel to side faces (504, 506) has an arc-shaped profile or a parabolic profile. Other suitable variations and configurations for this particular region of distal face (502) will be apparent to those of ordinary skill in the art in view of the teachings herein.

Curved surface (532) of pointed region (530) also curves along two planes (i.e., a plane that is parallel to upper and lower faces (508, 510) and a plane that is parallel to side faces (504, 506)) in this example. The curvature of curved surface (532) along one of those planes may be similar to the curvature of curved surface (532) along the other one of those planes. For instance, the curvature of curved surface (532) along the plane that is parallel to upper and lower faces (508, 510) may have an arc-shaped profile; while the curvature of curved surface (532) along the plane that is parallel to side faces (504, 506) may also have an arc-shaped profile. In such versions, the same radius length may be used to define the curves along these two planes. Alternatively, the radius length may differ for each plane. Similarly, the curvature of curved surface (532) along the plane that is parallel to upper and lower faces (508, 510) may have a parabolic profile; while the curvature of curved surface (532) along the plane that is parallel to side faces (504, 506) may also have a parabolic profile. The characteristics of the parabolas defining these curves may be the same or different from each other. As yet another merely illustrative example, the curvature of curved surface (532) along the plane that is parallel to upper and lower faces (508, 510) may have a hyperbolic profile; while the curvature of curved surface (532) along the plane that is parallel to side faces (504, 506) may also have a hyperbolic profile. The characteristics of the hyperbolas defining these curves may be the same or different from each other.

Of course, the curvature of curved surface (532) along the plane that is parallel to upper and lower faces (508, 510) may alternatively be of a completely different character than the curvature of curved surface (532) along the plane that is parallel to side faces (504, 506). For instance, the curvature of curved surface (532) along the plane that is parallel to upper and lower faces (508, 510) may have an arc-shaped profile; while the curvature of curved surface (532) along the plane that is parallel to side faces (504, 506) has a parabolic profile or a hyperbolic profile. As another merely illustrative example, the curvature of curved surface (532) along the plane that is parallel to upper and lower faces (508, 510) may have a parabolic profile; while the curvature of curved surface (532) along the plane that is parallel to side faces (504, 506) has an arc-shaped profile or a hyperbolic profile. As yet another merely illustrative example, the curvature of curved surface (532) along the plane that is parallel to upper and lower faces (508, 510) may have a hyperbolic profile; while the curvature of curved surface (532) along the plane that is parallel to side faces (504, 506) has an arc-shaped profile or a parabolic profile. Other suitable variations and configurations for curved surface (532) will be apparent to those of ordinary skill in the art in view of the teachings herein.

In the present example, the configuration of pointed region (530) may provide a very intense acoustic pressure at tip (534), which may cause initiation of microbubble formation for enhanced cavitation. In other words, tip (534) may generate "seed" microbubbles, which are then expanded by the surrounding pressure field that is focused at tip (534). In some versions tip (534), curved surface (532), and/or the rest of distal face (502) include(s) carbon, magnesium, and/or an artificial agent such as a surfactant, which may help generate cavitation. In some versions (534) is formed to present a flat distal surface. In some other versions, tip (534) is rounded. In still other versions, tip (534) is sacrificial. In still other versions, tip (534) is substantially sharp, formed by the natural convergence of curved surface (532). As yet another merely illustrative variation, tip (534) may include an orifice that is in fluid communication with a conduit that extends along the length of blade (500). This conduit and orifice may be used to communicate a gas through tip (534) to assist in microbubble seeding. In addition or in the alternative, the conduit and orifice may be used to communicate a liquid through tip (534) to assist in driving the microbubbles distally away from tip (534). Other suitable ways in which tip (534) may be formed and used will be apparent to those of ordinary skill in the art in view of the teachings herein.

D. Exemplary Ultrasonic Blade with Curved Distal Face and Fluid Conduit

Figure 14:
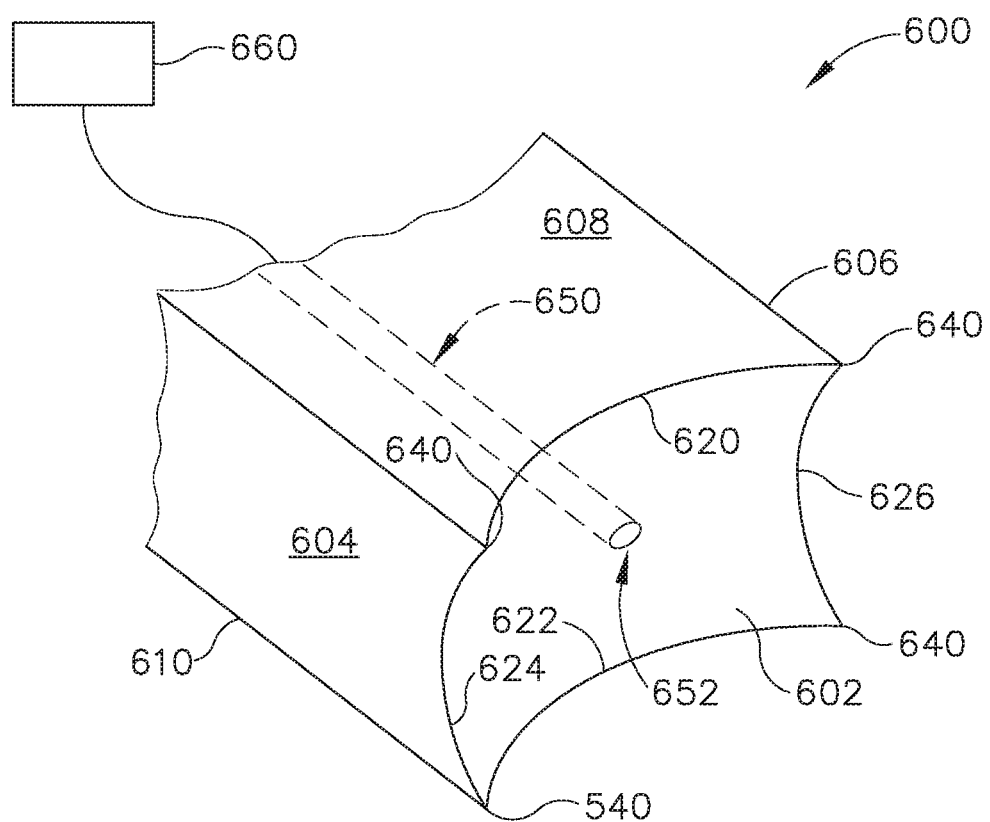
FIG. 14 depicts a perspective view of the distal end of another exemplary alternative ultrasonic blade that may be incorporated into the instrument of FIG. 2.

FIG. 14 shows another exemplary alternative ultrasonic blade (600) that may be readily incorporated into instrument (20, 120). In particular, blade (600) may be mechanically and acoustically coupled with waveguide (28, 128) in place of blade (24, 132). Blade (600) of this example comprises a curved distal face (602), flat side faces (604, 606), a flat upper face (608), and a flat lower face (610). It should be understood that any one or more of surfaces (604, 606, 608, 610) may instead by curved and/or have other characteristics.

The body of ultrasonic blade (600) defines a central longitudinal axis. This axis extends through a center, proximal-most point on curved distal face (602). In the present example, the curvature of distal face (602) provides a curved upper edge (620) at the transition between distal face (602) and upper face (608). The curvature of distal face (602) also provides a curved lower edge (622) at the transition between distal face (602) and lower face (610). Furthermore, the curvature of distal face (602) provides a curved lateral edge (624) at the transition between distal face (602) and side face (604); as well as a curved lateral edge (626) at the transition between distal face (602) and side face (606). Edges (620, 622) meet edges (624, 626) at sharp points (640). In some versions, points (640) are rounded, flattened, or otherwise shaped to avoid snagging on tissue or other structures.

It should be understood from the foregoing that distal face (602) curves along two planes (i.e., a plane that is parallel to upper and lower faces (608, 610) and a plane that is parallel to side faces (604, 606)) in this example. The curvature of distal face (602) along one of those planes may be similar to the curvature of distal face (602) along the other one of those planes. For instance, the curvature of distal face (602) along the plane that is parallel to upper and lower faces (608, 610) may have an arc-shaped profile; while the curvature of distal face (602) along the plane that is parallel to side faces (604, 606) may also have an arc-shaped profile. In such versions, the same radius length may be used to define the curves along these two planes. Alternatively, the radius length may differ for each plane. Similarly, the curvature of distal face (602) along the plane that is parallel to upper and lower faces (608, 610) may have a parabolic profile; while the curvature of distal face (602) along the plane that is parallel to side faces (604, 606) may also have a parabolic profile. The characteristics of the parabolas defining these curves may be the same or different from each other. As yet another merely illustrative example, the curvature of distal face (602) along the plane that is parallel to upper and lower faces (608, 610) may have a hyperbolic profile; while the curvature of distal face (602) along the plane that is parallel to side faces (604, 606) may also have a hyperbolic profile. The characteristics of the hyperbolas defining these curves may be the same or different from each other.

Of course, the curvature of distal face (602) along the plane that is parallel to upper and lower faces (608, 610) may alternatively be of a completely different character than the curvature of distal face (602) along the plane that is parallel to side faces (604, 606). For instance, the curvature of distal face (602) along the plane that is parallel to upper and lower faces (608, 610) may have an arc-shaped profile; while the curvature of distal face (602) along the plane that is parallel to side faces (604, 606) has a parabolic profile or a hyperbolic profile. As another merely illustrative example, the curvature of distal face (602) along the plane that is parallel to upper and lower faces (608, 610) may have a parabolic profile; while the curvature of distal face (602) along the plane that is parallel to side faces (604, 606) has an arc-shaped profile or a hyperbolic profile. As yet another merely illustrative example, the curvature of distal face (602) along the plane that is parallel to upper and lower faces (608, 610) may have a hyperbolic profile; while the curvature of distal face (602) along the plane that is parallel to side faces (604, 606) has an arc-shaped profile or a parabolic profile. Other suitable variations and configurations for distal face (602) will be apparent to those of ordinary skill in the art in view of the teachings herein.

Blade (600) of this example also defines an internal conduit (650) that terminates at an orifice (652) located at the center of distal face (602). Internal conduit (650) is in fluid communication with a fluid source (660). Fluid source (660) and conduit (650) may be used to communicate a gas to thereby introduce "seed" microbubbles at distal face (602) via orifice (652). Such seeded microbubbles may then be expanded by the pressure field that is generated by blade (600). In addition or in the alternative, fluid source (660) and conduit (650) may be used to communicate a fluid through distal face (602) via orifice (652). Such a communicated fluid may be used to assist in driving the microbubbles distally away from distal face (602). In addition, it should be understood that blade (600) may serve as an ultrasonic pump, driving the fluid distally through conduit (650) and orifice (652) by virtue of the ultrasonic vibrations of blade (600). For instance, at least a portion of conduit (650) may comprise an annulus that is tapered, opening/expanding toward orifice (652). As another merely illustrative example, a pump may be used to drive fluid through conduit (650). Such a pump may be interposed between fluid source (660) and conduit (650). In some instances, the fluid comprises saline. It should also be understood that the fluid may comprise a high surface tension fluid with or without bubbles. In addition or in the alternative, the fluid may comprise materials such as surfactants that may lower the threshold for cavitation (e.g., such that it is easier to cavitate in the liquid). Other suitable properties that may be incorporated into fluid from fluid source (660) will be apparent to those of ordinary skill in the art in view of the teachings herein. Similarly, other suitable features, configurations, and operabilities for blade (600) will be apparent to those of ordinary skill in the art in view of the teachings herein.

Figure 15:
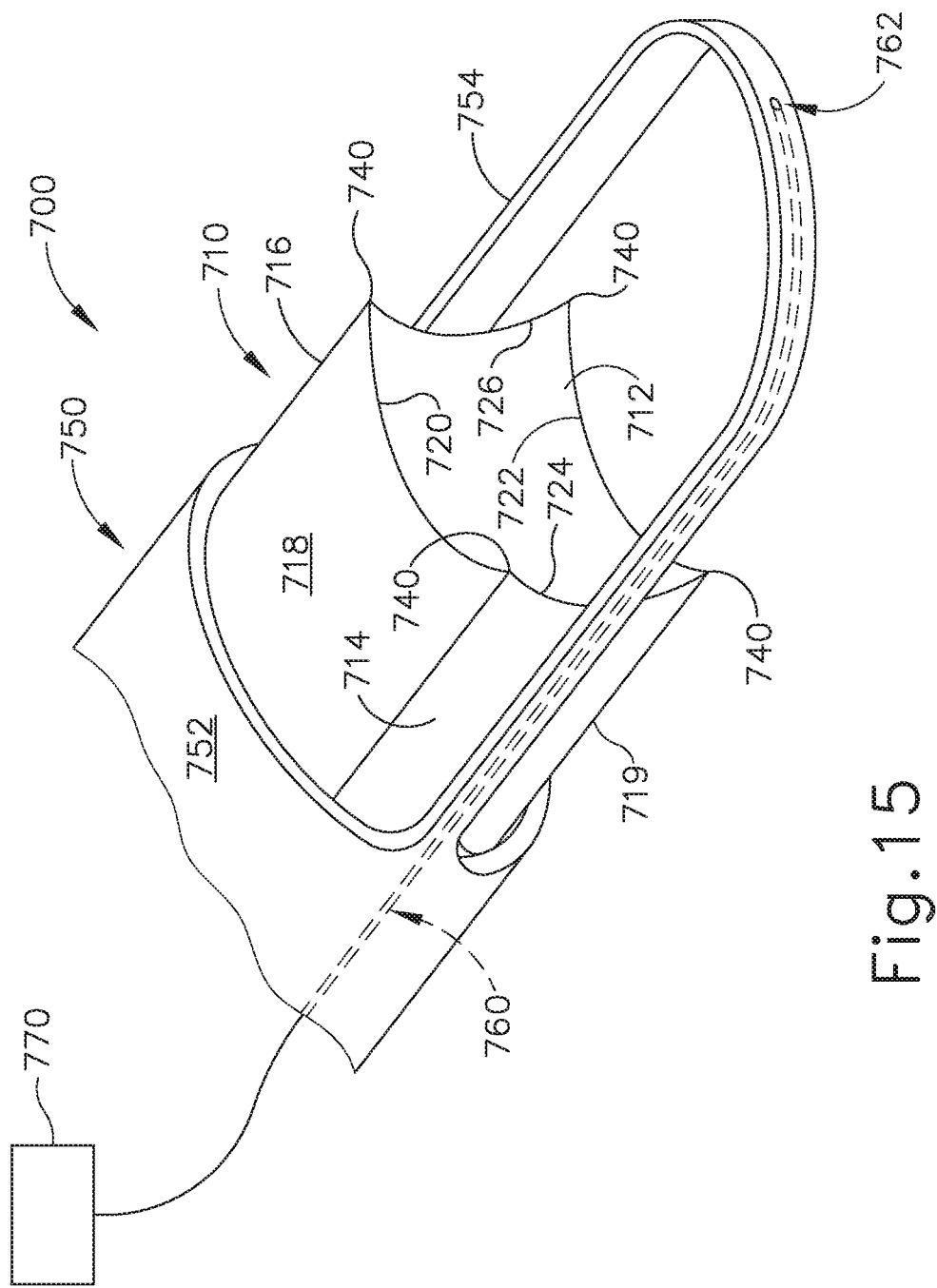
FIG. 15 depicts a perspective view of the distal end of another exemplary alternative ultrasonic blade that may be incorporated into the instrument of FIG. 2.

E. Exemplary Ultrasonic Blade with Curved Distal Face and Fluid Dispensing Feature FIG. 15 shows an exemplary alternative ultrasonic blade assembly (700) that may be readily incorporated into instrument (20, 120). Blade assembly (700) of this example comprises an ultrasonic blade (710) and a fluid dispensing feature (750). Blade (710) may be mechanically and acoustically coupled with waveguide (28, 128) in place of blade (24, 132). Blade (710) of this example is substantially identical to blade (600) described above. In particular, blade (710) comprises a curved distal face (712), flat side faces (714, 716), a flat upper face (718), and a flat lower face (719). It should be understood that any one or more of surfaces (714, 716, 718, 719) may instead by curved and/or have other characteristics.

The body of ultrasonic blade (710) defines a central longitudinal axis. This axis extends through a center, proximal-most point on curved distal face (712). In the present example, the curvature of distal face (712) provides a curved upper edge (720) at the transition between distal face (712) and upper face (718). The curvature of distal face (712) also provides a curved lower edge (722) at the transition between distal face (712) and lower face (710). Furthermore, the curvature of distal face (712) provides a curved lateral edge (724) at the transition between distal face (712) and side face (714); as well as a curved lateral edge (726) at the transition between distal face (712) and side face (716). Edges (720, 722) meet edges (724, 726) at sharp points (740). In some versions, points (740) are rounded, flattened, or otherwise shaped to avoid snagging on tissue or other structures.

It should be understood from the foregoing that distal face (712) curves along two planes (i.e., a plane that is parallel to upper and lower faces (718, 719) and a plane that is parallel to side faces (714, 716)) in this example. The curvature of distal face (712) along one of those planes may be similar to the curvature of distal face (712) along the other one of those planes. For instance, the curvature of distal face (712) along the plane that is parallel to upper and lower faces (718, 719) may have an arc-shaped profile; while the curvature of distal face (712) along the plane that is parallel to side faces (714, 716) may also have an arc-shaped profile. In such versions, the same radius length may be used to define the curves along these two planes. Alternatively, the radius length may differ for each plane. Similarly, the curvature of distal face (712) along the plane that is parallel to upper and lower faces (718, 719) may have a parabolic profile; while the curvature of distal face (712) along the plane that is parallel to side faces (714, 716) may also have a parabolic profile. The characteristics of the parabolas defining these curves may be the same or different from each other. As yet another merely illustrative example, the curvature of distal face (712) along the plane that is parallel to upper and lower faces (718, 719) may have a hyperbolic profile; while the curvature of distal face (712) along the plane that is parallel to side faces (714, 716) may also have a hyperbolic profile. The characteristics of the hyperbolas defining these curves may be the same or different from each other.

Of course, the curvature of distal face (712) along the plane that is parallel to upper and lower faces (718, 719) may alternatively be of a completely different character than the curvature of distal face (712) along the plane that is parallel to side faces (714, 716). For instance, the curvature of distal face (712) along the plane that is parallel to upper and lower faces (718, 719) may have an arc-shaped profile; while the curvature of distal face (712) along the plane that is parallel to side faces (714, 716) has a parabolic profile or a hyperbolic profile. As another merely illustrative example, the curvature of distal face (712) along the plane that is parallel to upper and lower faces (718, 719) may have a parabolic profile; while the curvature of distal face (712) along the plane that is parallel to side faces (714, 716) has an arc-shaped profile or a hyperbolic profile. As yet another merely illustrative example, the curvature of distal face (712) along the plane that is parallel to upper and lower faces (718, 719) may have a hyperbolic profile; while the curvature of distal face (712) along the plane that is parallel to side faces (714, 716) has an arc-shaped profile or a parabolic profile. Other suitable variations and configurations for distal face (712) will be apparent to those of ordinary skill in the art in view of the teachings herein.

Fluid dispensing feature (750) comprises a sheath (752) that is disposed about blade (710). In the present example, sheath (752) has a circular cross-sectional profile. Alternatively, the cross-sectional profile of sheath (752) may be elliptical, rectangular, or otherwise shaped. Fluid dispensing feature (750) further comprises an irrigation beam (754) extending distally from sheath (752). Irrigation beam (754) is U-shaped in this example, with the bend of the "U" being positioned distal to distal face (712). An internal conduit (760) extends through sheath (752) and into irrigation beam (754). Conduit (760) terminates at an orifice (762) located at the center of the bend of the "U." While conduit (760) is located internal to irrigation beam (754) in this example, it should be understood that conduit (760) may instead be located external to irrigation beam (754). By way of example only, conduit (760) may comprise a tube that is secured to the exterior of irrigation beam (754).

In the present example, orifice (762) is positioned and oriented upwardly on irrigation beam (754). In some other versions, orifice (762) is positioned and oriented distally on irrigation beam (754). In still other versions, orifice (762) is positioned and oriented proximally on irrigation beam (754). It should also be understood that irrigation beam (754) may include a plurality of orifices (762). The orifices (762) of such a plurality may be located at different orientations at the center of the bend of the "U" (e.g., one oriented distally, one oriented upwardly, etc.). In addition or in the alternative, orifices (762) of a plurality may be located at different positions along the length of irrigation beam (754). Other suitable configurations, positions, and orientations for one or more orifices (762) will be apparent to those of ordinary skill in the art in view of the teachings herein. It should also be understood that irrigation beam (754) need not necessarily be "U" shaped. By way of example only, irrigation beam (754) may be "V" shaped, shaped like a partial rectangle, or otherwise shaped. Other suitable configurations for irrigation beam (754) will be apparent to those of ordinary skill in the art in view of the teachings herein.

Internal conduit (760) is in fluid communication with a fluid source (770). Fluid source (770) and conduit (760) may be used to communicate a gas to thereby introduce "seed" microbubbles distal to at distal face (712) via orifice (762). Such seeded microbubbles may then be expanded by the pressure field that is generated by blade (710). In addition or in the alternative, fluid source (770) and conduit (760) may be used to communicate a fluid through irrigation beam (754) via orifice (762). Such a communicated fluid may be used to assist in driving the microbubbles distally away from distal face (712). In some instances, the fluid comprises saline. It should also be understood that the fluid may comprise a high surface tension fluid with or without bubbles. In addition or in the alternative, the fluid may comprise materials such as surfactants that may lower the threshold for cavitation (e.g., such that it is easier to cavitate in the liquid). Other suitable properties that may be incorporated into fluid from fluid source (770) will be apparent to those of ordinary skill in the art in view of the teachings herein. Similarly, other suitable features, configurations, and operabilities for blade assembly (700) will be apparent to those of ordinary skill in the art in view of the teachings herein.

IV. Exemplary Control Algorithm to Enhance Cavitation

As noted above, a generator (12) may be used to power an ultrasonic transducer (26), which in turn drives an ultrasonic blade (24) to vibrate ultrasonically. It should be understood that the power profile communicated by generator (12) may be controlled to selectively vary the ultrasonic vibrations of a blade (24). For instance, in versions of a surgical system (10) where one of blades (200, 300, 400, 500, 600, 710) is used, generator (12) may provide a power profile that ultimately causes blade (200, 300, 400, 500, 600, 710) to vibrate in a manner that promotes desired cavitation effects. In other words, the desired cavitation effects may be provided by a combination of the structural configuration of blade (200, 300, 400, 500, 600, 710) and the power profile that is used to power the ultrasonic transducer (26) that drives blade (200, 300, 400, 500, 600, 710). Such a power profile may include features configured to create "seed" microbubbles and features configured to grow those microbubbles to the point where the microbubbles collapse on the targeted tissue to produce the desired cavitation effects. Such power profiles may be provided in accordance with a control logic in generator (12). Various suitable ways in which such a control logic may be provided within generator (12) will be apparent to those of ordinary skill in the art in view of the teachings herein.

Figure 16:
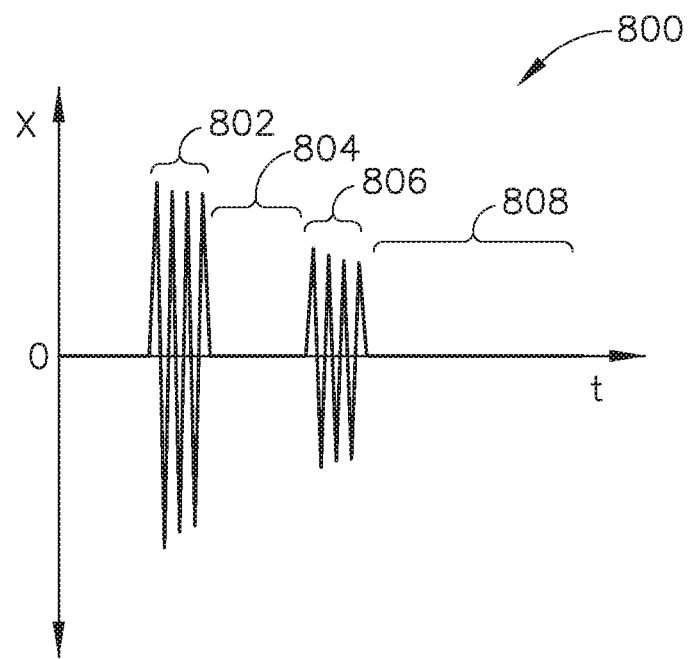
FIG. 16 depicts a plot of ultrasonic blade displacement as a function of time in accordance with a first exemplary control algorithm that may be used to operate the system of FIG. 1.

FIG. 16 shows an exemplary ultrasonic vibrational profile (800) that may be provided through a transducer (26) and blade (200, 300, 400, 500, 600, 710), based on a power profile from a generator (12) that is configured to promote cavitation. In this example, a first vibration set (802) is provided during a first period of time. This vibration set (802) has a relatively high amplitude and only lasts for a relatively brief period of time. The amplitude of vibrations in the first vibration set (802) is substantially consistent throughout the first period of time. This first vibration set (802) is configured to generate "seed" microbubbles in the fluid acted upon by blade (200, 300, 400, 500, 600, 710). The first vibration set (802) is followed by a first vibrational pause (804), which lasts for a second period of time. This first vibrational pause (804) may allow the generated microbubbles to stabilize. This first vibrational pause (804) is then followed by a second vibration set (806), which lasts for a third period of time. This second vibration set (806) has a lower amplitude than the first vibration set (802). In addition or in the alternative, the second vibration set (806) may have a different frequency from first vibration set (802) (e.g., a higher frequency or lower frequency than first vibration set (802)). The amplitude of vibrations in the second vibration set (806) is substantially consistent throughout the third period of time. The second vibration set (806) is configured to grow the microbubbles in the fluid acted upon by blade (200, 300, 400, 500, 600, 710). In some versions, the third period of time is longer than the first period of time, such that the second vibration set (806) has a greater duration than the first vibration set (802).

The second vibration set (806) is followed by a second vibrational pause (808), which lasts for a fourth period of time. This second vibrational pause (808) may provide a decrease in the gross circulation of the fluid acted upon by blade (200, 300, 400, 500, 600, 710), which may prevent microbubbles from being otherwise swept away from the target tissue. The second vibrational pause (808) has a longer duration than the first vibrational pause (804) in this example. Alternatively, pauses (804, 806) may have the same duration; or second vibrational pause (808) may have a shorter duration than the first vibrational pause (804). The duration of either or both of pauses (804, 806) may be adjusted to reduce any undesired thermal effects.

After the second vibrational pause (808), the above process may be repeated. Alternatively, another vibration set like second vibration set (806) may be applied to further grow the microbubbles. As yet another merely illustrative alternative, a third vibration set (not shown) having an amplitude like second vibration set (806) but lasting for a longer period of time may be provided to further ensure bursting of the microbubbles. Such bubble-growing vibration sets may be repeated as many times as desired, with pauses of any suitable duration between the bubble-growing vibration sets, before starting the process over again with a seeding vibration set like first vibration set (802).

Figure 17:
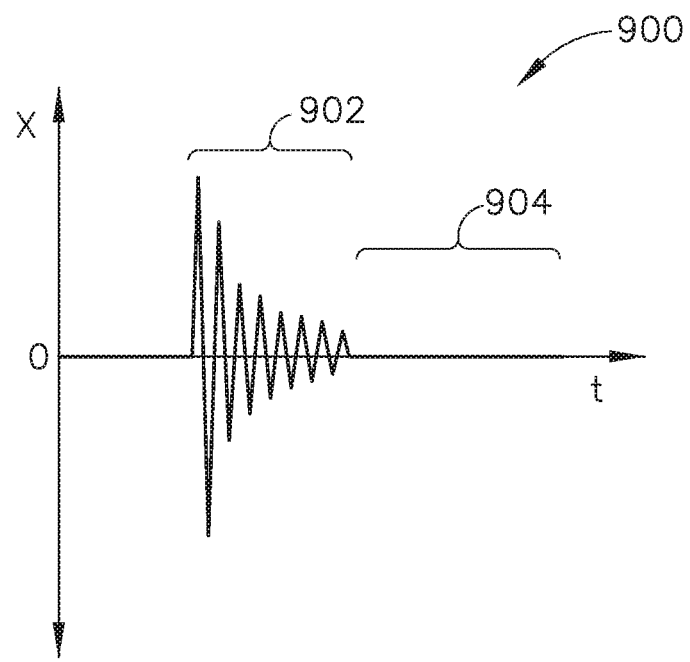
FIG. 17 depicts a plot of ultrasonic blade displacement as a function of time in accordance with a second exemplary control algorithm that may be used to operate the system of FIG. 1.

FIG. 17 shows another exemplary ultrasonic vibrational profile (900) that may be provided through a transducer (26) and blade (200, 300, 400, 500, 600, 710), based on a power profile from a generator (12) that is configured to promote cavitation. In this example, a vibration set (902) is provided during a first period of time. This vibration set (902) starts with a relatively high amplitude that decays to a lower amplitude, ultimately decaying into a zero amplitude. In some instances the vibration frequency also either decays or steps down during the life of vibration set (902). During the high amplitude stage of vibration set (902), vibration set (902) may generate "seed" microbubbles in the fluid acted upon by blade (200, 300, 400, 500, 600, 710). During the lower amplitude stage of vibration set (902), vibration set (902) may grow the microbubbles in the fluid acted upon by blade (200, 300, 400, 500, 600, 710). Thus, the high amplitude stage of vibration set (902) may be similar to first vibration set (802) described above; while the low amplitude stage of vibration set (902) may be similar to second vibration set (806) described above. It should be understood that the transition from high amplitude to low amplitude may be so gradual in vibration set (902) that there is no clearly demarcated transition point. It should also be understood that the high or low amplitude may extend through any part of the first period of time. For instance, amplitude values associated with seeding microbubbles may last for a shorter duration than amplitude values associated with growing microbubbles.

After the amplitude of vibration set (902) reaches zero upon expiration of the first period of time, a vibrational pause (904) is provided in order to decrease gross circulation in the fluid acted upon by blade (200, 300, 400, 500, 600, 710), which may prevent microbubbles from being otherwise swept away from the target tissue. The vibrational pause (904) lasts for a second period of time. After the vibrational pause (904), the above process may be repeated. Alternatively, a low amplitude vibration set (e.g., similar to second vibration set (806)) may be applied to further grow the microbubbles. As yet another merely illustrative alternative, a third vibration set (not shown) having an amplitude like second vibration set (806) but lasting for a longer period of time may be provided to further ensure bursting of the microbubbles. Such bubble-growing vibration sets may be repeated as many times as desired, with pauses of any suitable duration between the bubble-growing vibration sets, before starting the process over again with a vibration set like vibration set (902). Other suitable variations of ultrasonic vibrational profiles (800, 900) will be apparent to those of ordinary skill in the art in view of the teachings herein.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of providing cavitation in a tissue or other anatomical structure at a surgical site in a patient, the method comprising:
    (a) activating an ultrasonic element at a first vibrational profile to generate microbubbles in a fluid at a surgical site in a patient; and
    (b) activating the ultrasonic element at a second vibrational profile to grow the microbubbles and burst the microbubbles, to thereby induce erosion by cavitation in the tissue or other anatomical structure at the surgical site;
    wherein the first vibrational profile includes ultrasonic vibrations at a first amplitude;
    wherein the second vibrational profile includes ultrasonic vibrations at a second amplitude;
    wherein the first amplitude is greater than the second amplitude.

2. The method of claim 1, further comprising introducing the fluid to the surgical site from an external fluid source.

3. The method of claim 2, wherein the fluid is introduced to the surgical site from an external fluid source via the ultrasonic element.

4. The method of claim 1, further comprising maintaining the first vibrational profile for a first activation duration.

5. The method of claim 4, wherein the ultrasonic element is vibrated substantially consistently at the first amplitude throughout the first activation duration.

6. The method of claim 4, further comprising maintaining the second vibrational profile for a second activation duration.

7. The method of claim 6, wherein the second activation duration is longer than the first activation duration such that the second vibrational profile is activated for a longer duration than the first vibrational profile.

8. The method of claim 4, further comprising ceasing activation of the ultrasonic element for a first pause duration after the first activation duration.

9. The method of claim 8, wherein the first pause duration allows the microbubbles generated by the first vibrational profile to stabilize.

10. The method of claim 9, further comprising ceasing activation of the ultrasonic element for a second pause duration after activating the ultrasonic element at the second vibrational profile.

11. The method of claim 10, wherein ceasing activation of the ultrasonic element for the second pause duration decreases the circulation of the fluid which prevents the microbubbles from being swept away from the surgical site.

12. The method of claim 10, wherein the second pause duration is longer than the first pause duration.

13. The method of claim 10, wherein the second pause duration is the same duration as the first pause duration.

14. The method of claim 10, wherein the second pause duration is shorter than the first pause duration.

15. The method of claim 10, further comprising adjusting the first and second pause durations to reduce thermal effects.

16. The method of claim 10, further comprising activating a third vibrational profile to further grow the microbubbles after the second pause duration, wherein the third vibrational profile has a third amplitude that is equivalent to the second amplitude.

17. The method of claim 16, further comprising:
(a) maintaining the second vibrational profile for a second activation duration; and
(b) maintaining the third vibrational profile for a third activation duration, wherein the third activation duration is longer than the second activation duration of time.

18. A method of providing cavitation in a tissue or other anatomical structure at a surgical site in a patient, the method comprising:
(a) activating an ultrasonic element at a high amplitude to generate microbubbles in a fluid at a surgical site in a patient;
(b) transitioning the ultrasonic element from the high amplitude to a low amplitude to grow and burst the microbubbles in the fluid at the surgical site, wherein transitioning the ultrasonic element from the high amplitude to the low amplitude is gradual, wherein activating the ultrasonic element at the low amplitude induces erosion by cavitation in the tissue or other anatomical structure at the surgical site;
(c) transitioning the ultrasonic element from the low amplitude to a zero amplitude; and
(d) maintaining an inactivity period at the zero amplitude to decrease gross circulation in the fluid to prevent the microbubbles from being swept away from the surgical site.

19. The method of claim 18, wherein the ultrasonic element is activated at the high amplitude for a shorter duration than at the low amplitude.

20. A method of providing cavitation in a tissue or other anatomical structure at a surgical site in a patient, the method comprising:
(a) initiating a first vibration period, wherein the first vibration period comprises:
(i) activating an ultrasonic element at a high amplitude to generate microbubbles in a fluid at a surgical site in a patient,
(ii) transitioning the ultrasonic element from the high amplitude to a low amplitude to grow and burst the microbubbles in the fluid at the surgical site, wherein transitioning the ultrasonic element from the high amplitude to the low amplitude is gradual, wherein activating the ultrasonic element at the low amplitude induces erosion by cavitation in the tissue or other anatomical structure at the surgical site, and
(iii) transitioning the ultrasonic element from the low amplitude to a zero amplitude;
(b) initiating an inactivity period after reaching the zero amplitude to decrease gross circulation in the fluid to prevent the microbubbles from being swept away from the surgical site; and
(c) initiating a second vibration period, wherein the second vibration period comprises:
(i) activating the ultrasonic element at the low amplitude to further grow the microbubbles, and
(ii) transitioning the ultrasonic element from the low amplitude to the zero amplitude,
wherein the second vibration period is longer than the first vibration period.

* * * * *